(12) United States Patent
Teagarden et al.

(10) Patent No.: US 7,829,100 B2
(45) Date of Patent: Nov. 9, 2010

(54) PHARMACEUTICAL COMPOSITION HAVING MODIFIED CARRIER

(76) Inventors: Dirk L. Teagarden, 4062 Prestwick Dr., Kalamazoo, MI (US) 49002; Nancy J. Britten, 4750 Norfolk Cir., Portage, MI (US) 49024; Scott A. Brown, 9800 Firefly, Galesburg, MI (US) 49053; James F. Caputo, 215 Brittany Dr., Portage, MI (US) 49002; Leslie C. Eaton, 11126 E. Higley Cir., Schoolcraft, MI (US) 49087; Ondrej Hendl, 7541 Woodcrest Rd., Portage, MI (US) 49024; Syed F. Huda, 245 E. Harcourt, #A, Saginaw, MI (US) 48609; Harry M. King, 2623 Beethoven Ave., Portage, MI (US) 49024-6617; Susan M. Machkovech, 10557 W. P Ave., Mattawan, MI (US) 49071; Randal Lee Schapaugh, 178 Moonwood Trail, Battle Creek, MI (US) 49014; Stanley M. Speaker, 5404 Azalea, Portage, MI (US) 49002; Jean M. Steele, 2682 Sleepy Hollow Dr., Portage, MI (US) 49024; Ching-Chiang Su, 8373 Canary Dr., Kalamazoo, MI (US) 49009; Terry R. Urban, 1828 Haverhill Ave., Portage, MI (US) 49024; Niki A. Waldron, 2460 Wildemere, Kalamazoo, MI (US) 49009; Monica L. Whitmire, 1190 N. 5th St., Kalamazoo, MI (US) 49009

( * ) Notice: Subject to any disclaimer, the term of this patent is extended or adjusted under 35 U.S.C. 154(b) by 1042 days.

(21) Appl. No.: 10/704,989

(22) Filed: Nov. 10, 2003

(65) Prior Publication Data

US 2004/0142027 A1   Jul. 22, 2004

Related U.S. Application Data

(63) Continuation-in-part of application No. 09/948,827, filed on Sep. 7, 2001, now abandoned.

(60) Provisional application No. 60/231,767, filed on Sep. 12, 2000.

(51) Int. Cl.
 A61K 31/545  (2006.01)
 A61K 39/12   (2006.01)
(52) U.S. Cl. .................. 424/204.1; 424/450; 514/12
(58) Field of Classification Search ............... None
 See application file for complete search history.

(56) References Cited

U.S. PATENT DOCUMENTS

| 4,297,353 A |   | 10/1981 | Maulding ............ 424/365 |
| 5,013,713 A |   | 5/1991  | Mitchell |
| 5,019,395 A |   | 5/1991  | Mahjour et al. ........ 424/449 |
| 5,162,057 A |   | 11/1992 | Akiyama et al. ........ 106/203 |
| 5,721,359 A | * | 2/1998  | Dunn et al. ............ 540/227 |
| 5,736,151 A | * | 4/1998  | Foster et al. ........... 424/423 |
| 5,739,159 A |   | 4/1998  | Wolf .................. 514/475 |
| 6,074,657 A | * | 6/2000  | Brown ................. 424/423 |

FOREIGN PATENT DOCUMENTS

| WO | WO 94/00105  | 1/1994 |
| WO | WO 96/20698  | 7/1996 |
| WO | WO 97/49402  | 12/1997 |
| WO | WO 98/41207  | 9/1998 |

OTHER PUBLICATIONS

Matheson Tri-Gas, Inc. Ethylene Oxide MSDS. Downloaded Dec. 22, 2006 from http://www.thesontrigas.com/pdfs/msds/MAT09520.pdf.
Remington, The Science and Practice of Pharmacy. 20th Edition, p. 765, 2000.

* cited by examiner

*Primary Examiner*—Christopher R. Tate
*Assistant Examiner*—Roy Teller
(74) *Attorney, Agent, or Firm*—John H. Engelmann; Lucy X. Yang

(57) ABSTRACT

A composition comprising:
(a) one to three bioactive agents; and
(b) a modified liquid vehicle;
wherein immediately after manufacture of the composition, said composition can be administered to a host such that the one to three bioactive agents is released to the host on a sustained basis is provided.

13 Claims, 1 Drawing Sheet

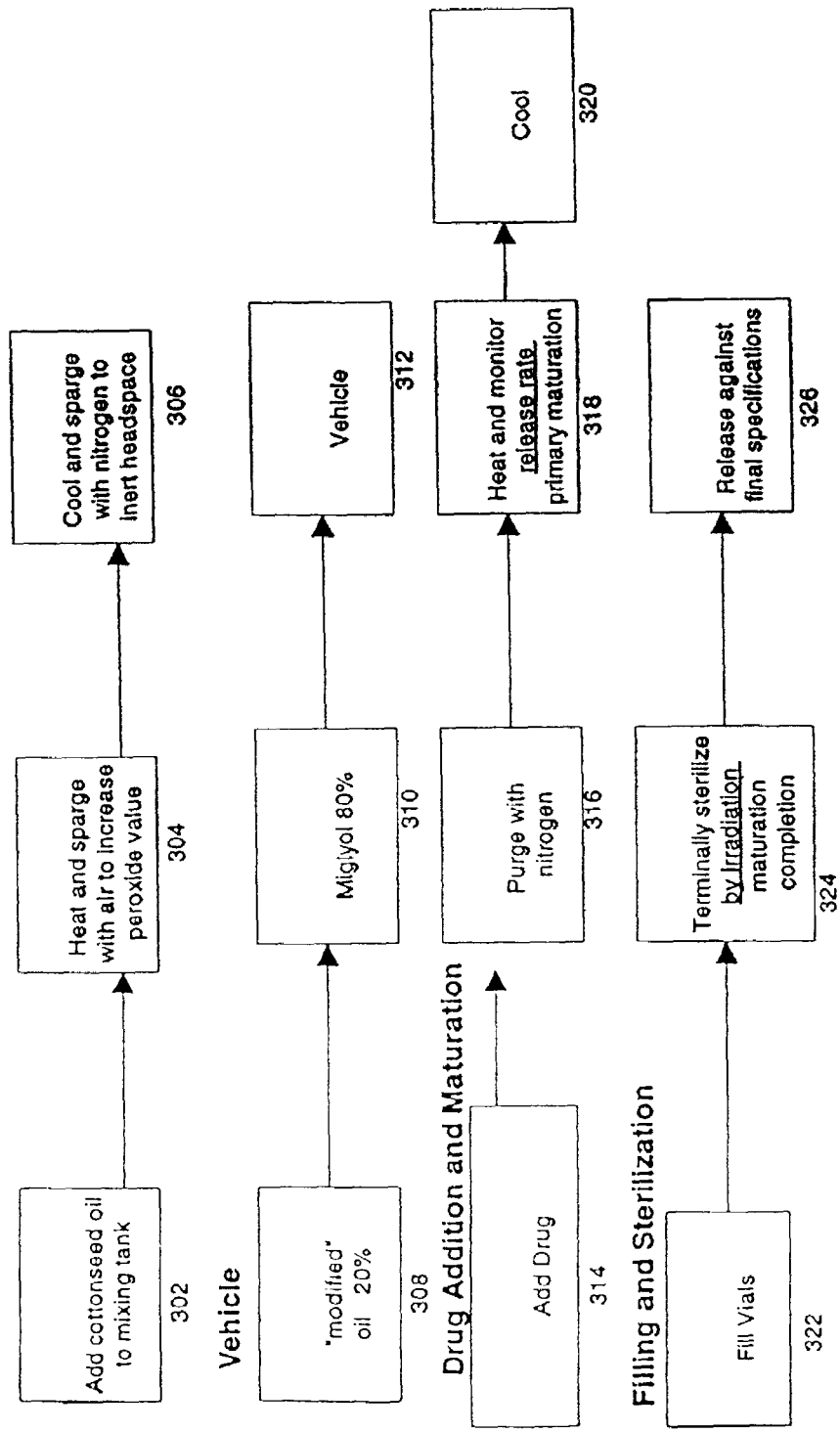

PHARMACEUTICAL COMPOSITION HAVING MODIFIED CARRIER

CROSS-REFERENCE TO RELATED APPLICATIONS

This application is a continuation-in-part of U.S. Ser. No. 09/948,827, filed Sep. 7, 2001 now abandoned, which claims the benefit of U.S. Ser. No. 60/231,767, filed Sep. 12, 2000, under 35 USC 119(e)(i), incorporated by reference in their entirety.

BACKGROUND OF THE INVENTION

1. Field of the Invention

The present invention relates to pharmaceutical compositions. More specifically, it relates to the use of modified pharmaceutically acceptable liquid carriers that provide the composition with predictable sustained-release properties.

2. Background of the Invention

In the pharmaceutical arts, drug delivery is an element as significant as drug activity. Many drugs or bioactive agents with apparent in vitro activity fail at the clinical level due to the inability to prepare, store, or deliver the bioactive agent to the site of action in effective concentrations over a sufficient period of time.

A vehicle for the stable storage and effective delivery profile of a bioactive agent is of great utility. Those skilled in the art will understand that storage stability and effective delivery profile are, to some extent, specific to bioactive agents, the condition for which the bioactive agent is administered, and the presenting condition of the subject.

Sustained-release or oil-based preparations are considered in WO97/49402 (Vlaminck); WO94/00105 (Sabater); U.S. Pat. No. 4,297,353 (Hawkins); U.S. Pat. No. 5,019,395 (Mahjour); U.S. Pat. No. 5,739,159 (Wolf); U.S. Pat. No. 5,162,057 (Akiyama); WO96/20698 (Levy) the teachings of which are incorporated herein by reference. Also incorporated by reference is WO98/41207 (Brown) addressing subcutaneous (S.C.) administration of antibiotic into the ear of an animal.

U.S. Pat. No. 5,721,359 discloses the molecule crystalline ceftiofur free acid (CCFA), which is a cephalosporin antibiotic intended for use in mammals, and in particular food animals (e.g., cattle, sheep, goats and swine). The patent suggests that oil suspensions of CCFA can be produced for administration to food animals where the oils are vegetable oils. The oils as disclosed in the patent are intended to be used in their natural form. An advantage touted by this molecule over other antibiotics, particularly those in the ceftiofur family is the ability for CCFA to yield a sustained-release pharmaceutical composition. It has now been discovered that the sustained-release profile is not readily predictable and reproducible in immediate post-production product that uses natural vegetable oils.

Despite the above teachings, there still exists a need in the art for pharmaceutical compositions that can be administered on a sustained-release basis and wherein the release performance is predictable and reproducible immediately after manufacture of the product.

BRIEF SUMMARY OF THE INVENTION

In accordance with the present invention a novel pharmaceutical composition that can be administered on a sustained-release basis and wherein the release performance is predictable immediately after manufacture of the product is provided. More specifically, the predictable performance is obtained by using a modified liquid carrier.

One embodiment of the invention provides a pharmaceutical composition comprising:

(a) one to three bioactive agents; and (b) a modified liquid vehicle;

wherein immediately after manufacture of the composition, said composition can be administered to a host such that the one to three bioactive agents are released to the host on a predictable sustained-release basis.

In preferred embodiments, component (a) comprises CCFA and component (b) comprises a modified unsaturated oil optionally combined with a non-oxidizable oil. In particularly preferred embodiments component (b) comprises a mixture of a modified unsaturated oil with a natural saturated oil, and even more preferably a mixture of modified cottonseed oil with saturated coconut oil.

Another embodiment of the present invention provides a method for producing a pharmaceutical composition comprising the step of modifying a liquid vehicle and combining said modified liquid vehicle with a bioactive substance. According to this method the liquid vehicle is modified by the use of chemical, physical or mechanical means to produce a carrier that has a higher level of oxidation products as compared to its original, or non-modified form. Particularly preferred embodiments comprise the use of a combination of heat and gamma radiation. In addition, the modification step of this process may occur either prior to, after or both prior to and after the combining step.

A more specific aspect of this method comprises the steps of:

(a) heating natural cottonseed oil to increase its oxidation products and yield a modified cottonseed oil;

(b) combining said modified cottonseed oil with saturated coconut oil or saturated coconut oil products to yield a vehicle; and (c) adding crystalline ceftiofur free acid to said vehicle; and, optionally, thereafter;

(d) heating said pharmaceutical composition;

(e) cooling said composition;

(f) filling one or more vials with said composition; and (g) exposing said one or more vials to gamma radiation.

A further embodiment of the present invention provides the composition of the present invention for use in medical treatment.

An additional embodiment of the present invention provides the use of the inventive composition to prepare a medicament for treating or preventing a disease in a mammal.

A final embodiment of the present invention provides a method of treating or preventing a disease comprising administering to a mammal in need of such treatment an effective amount of the inventive composition. A preferred aspect of this invention is to treat bacterial infections in food animals or companion animals with an inventive CCFA composition.

An object of the present invention is to provide a novel sustained-release composition.

Still another object of the present invention is to provide a method for producing a novel sustained-release composition.

A further object of the present invention is to provide a method for treating a disease or condition in a mammal.

These, and other objects, will readily be apparent to those skilled in the art as reference is made to the drawings and detailed description of the preferred embodiment.

BRIEF DESCRIPTION OF THE DRAWINGS

FIG. 1 is a diagram of a method that can be used to produce the inventive compositions.

DETAILED DESCRIPTION OF THE INVENTION

In describing the preferred embodiment, certain terminology will be utilized for the sake of clarity. Such terminology is intended to encompass the recited embodiment, as well as all technical equivalents which operate in a similar manner for a similar purpose to achieve a similar result.

1. Terminology Definitions

This invention will be better understood with reference to the following definitions:

"Bioactive substances" shall be broadly understood to mean pharmaceuticals, immunogenic and immunomodulator compositions (including adjuvants), vectors such as liposomes and live vectors such as plasmids, viruses, spores, nutritional supplements and bacteria and mixtures thereof.

These include, but are not limited to, anti-infectives (e.g., antibiotics, antifungals, anti-virals), antineoplastics (e.g., anticancer agents, such as cis-platinum compounds), immunomodulators (e.g., antihistamines, immunoenhancers and immunosupressors), gastrointestinal sedatives, antacids, anti-inflammatory substances, vasodilators (coronary, cerebral and peripheral), anti-emetics, growth promoters, anti-obesity drugs, anthelmintics, hormones, vaccines, and any mixtures thereof. Specifically preferred bioactive agents include, but are not limited to, ceftiofur, including crystalline ceftiofur free acid (CCFA), platinum compounds (e.g., cis-platinum), ibuprofen, piroxicam, 1-[2-(4-fluorobenzoyl)aminoethyl]-4-(7-methoxynaphthyl) piperazine hydrochloride (FAMP), camptothecin, paclitaxel, flucytosine, cyclooxygenase-II inhibitors (e.g., coxibs and chromenes) and quinine.

"Sustained-delivery or Sustained-release" as used in relation to bioactive substances shall mean continued release or distribution of the bioactive substance such that the amount of bioactive remains in the patient's blood levels at a concentration of greater than a certain value (that value being one that produces therapeutically effective blood levels of active substance) over an extended period of time. The effective sustained-release blood levels desired would, of course, differ depending on the bioactive substance, the disease being treated, the patient, and the like, is considered to be known to the skilled artisan and can be determined by routine experimentation. More specifically, a sustained-delivery vehicle differs from an immediate-delivery vehicle in that the immediate-delivery vehicle releases its bioactive material at faster rate then the sustained-delivery vehicle, potentially requiring more administrations of bioactive per treatment regimen. For example, if the bioactive substance is ceftiofur crystalline free acid (CCFA), the desired level of ceftiofur metabolites in the patient's blood plasma is noted to be maintained at or above about 0.2 µg/ml. In one embodiment of the invention, a single dose of sustaining-vehicle CCFA maintains a ceftiofur metabolite level in the blood plasma of at or above about 0.2 µg/ml for at least three and preferably at least about four and more preferably at least about five days post-administration (sustained delivery of CCFA). Comparisons as to the degree of sustained delivery are made with equivalent bioactive agents. That is, sodium salts to sodium salts and free bases to free bases. Sustained-delivery as used in this document is to be specifically reconciled with the regulatory definition for the same term that requires that the concentration versus time profile have three distinct phases (i.e., an increasing concentration phase, a plateau phase and a concentration depletion phase). While the term sustained-delivery as used in this document may encompass the above regulatory definition it is not intended to be limited to it as compositions which are sustained delivery as defined herein need not possess the three distinct phases (e.g., the composition may have an increasing concentration phase and an extended concentration depletion phase).

"Liquid vehicles" include a modified unsaturated oil optionally combined with a non-oxidizable oil. Examples of unsaturated oils include naturally occurring oils such as castor oil, safflower oil, cottonseed oil, corn oil, olive oil, cod liver oil, almond oil, avocado oil, palm oil, sesame oil, peanut oil, and soybean oil. By way of example, cottonseed oil is available in a preparation of 70% unsaturated fatty acids (Sigma, St. Louis, Mo.). Examples of non-oxidizable oils include esters of medium to large chain fatty acids (e.g., fatty acid triglycerides with a chain length of about $C_6$ to about $C_{24}$). Mixtures of fatty acids are split from the natural oil (e.g., coconut oil, palm kernel oil, babassu oil, etc.) and are refined. In some embodiments, about $C_8$ to about $C_{12}$ fatty acid medium chain triglycerides (MCT) are useful. These saturated vehicles are comprised of capric acid (about 20 to about 45%) and caprylic acid (about 45 to about 80%). Examples of non-oxidizable oils also include saturated coconut oil (which typically includes a mixture of lauric, myristic, palmitic, capric and caprylic acids), including those sold under the MIGLYOL trademark from Huls and bearing trade designations 810, 812, 829 and 840. Also noted are the NeoBeeR™ products sold by Drew Chemicals. Isopropyl myristate is another example of a non-oxidizable oil of the current invention. Examples of non-oxidizable synthetic oils include tri-glycerides, or propylene glycol di-esters of saturated fatty acids having from 6 to 24 carbon atoms. Such carboxylic acids are meant to comprise those carboxylic acids having from 6 to 24 carbon atoms such as, for example hexanoic acid, octanoic (caprylic), nonanoic (pelargonic), decanoic (capric), undecanoic, lauric, tridecanoic, tetradecanoic (myristic), pentadecanoic, hexadecanoic (palmitic), heptadecanoic, octadecanoic (stearic), nonadecanoic, nonadecanoic, eicosanoic, heneicosanoic, docosanoic and lignoceric acid. Examples of oxidizable synthetic oils include tri-glycerides, or propylene glycol di-esters of unsaturated fatty acids having from 6 to 24 carbon atoms. Examples of unsaturated carboxylic acids include oleic, linoleic, linolenic acid and the like. It is understood that the tri-glyceride vehicle may include the mono-, di-, or triglyceryl ester of the fatty acids or mixed glycerides and/or propylene glycol di-esters wherein at least one molecule of glycerol has been esterified with fatty acids of varying carbon atom length.

"Modified" and "modification" as to the vehicles of this invention and as used in the claims shall be understood to define a vehicle which, through physical, chemical or mechanical means, has been altered as compared to its natural (or "non-modified" in the case of synthetic liquid carriers) form such that the modified vehicle has an increased level of oxidation products. Modification can be accomplished by heat modification, irradiation and/or exposure to energy sources (e.g., light, ultraviolet, infrared, gamma, X-ray or microwave radiation), addition of catalysts (i.e., t-butyl peroxide), the incorporation of specific triglycerides and their hydroperoxides, incorporation of polymeric species, incorporation of crosslinkers or of polymerization causing agents, oxidation regimens and combinations of these methods. These steps can be taken before or after addition of the drug to the vehicle, or both before and after addition of drug to the vehicle. In accordance with preferred embodiments of the present invention, the modification takes place in connection with the pharmaceutically acceptable liquid oils which are unsaturated.

"Substantially peroxidized unsaturated oil vehicle" shall refer to a modified liquid vehicle having a peroxide value of between about 0.1 and about 600, and in some embodiments about 10, about 20, about 40, or about 80 or any value in between. As used herein, peroxide values are expressed as milliequivalents (mEq) of peroxide per 1000 grams of oil sample. Peroxide value is conveniently measured by American Oil Chemists' Society (AOCS) (Official Method Cd 8-53) (Official Monographs, Soybean Oil, page 1434) manual titration, the teachings of which are incorporated herein by reference.

2. The Invention

The present invention comprises a composition comprising:

(a) one to three bioactive agents; and (b) a modified liquid vehicle;

wherein immediately after manufacture of the composition, said composition can be administered to a host such that the one to three bioactive agents is released to the host on a sustained basis.

It is a substantial advantage to identify a dosage form and method of preparation of a dosage form that provides sustained-release capability immediately upon production and maintains that release profile during a substantial storage period. In the present invention, a combination of preparatory steps and vehicle compositions are defined which yield sustained-release formulations upon processing. This is obtained by the use of a modified liquid vehicle, which can be in the form of a modified unsaturated oil and, optionally, a non-oxidizable oil in combination with the bioactive agent. In all embodiments, a key feature is that a portion of the vehicle has been modified either before, after or both before and after it has been combined with the bioactive agent.

The bioactive agents for use are as defined above. A preferred bioactive agent is crystalline ceftiofur free acid (CCFA) which is useful as an antibiotic drug compound in pharmaceutical dosage forms for treating valuable mammalian animals and humans suffering from bacterial infections. In particular embodiments, sustained-release ceftiofur free acid is useful as a veterinary antibiotic drug to treat animals such as cattle, swine, horses, sheep, goats, dogs, poultry and cats. Such treatment fights the effects of bacterial infections caused by susceptible organisms, such as *Pasteurella haemolytica* (*Mannheimia* Spp.), *Pasteurella multocida*, *Salmonella typhimurium, Salmonella choleraesuis, Actinobacillus pleuropneumoniae, Streptococcus suis, Streptococcus equi* (zooepidemicus), and other *Streptococcus* bacteria, *Haemophilus somnus, Escherichia coli, Staphylococcus aureus* and the like, as well as applicable anaerobic infections, such as *Fusobacterium necrophorum*. These types of infections are commonly associated with diseases in animals, such as bovine respiratory disease and swine respiratory disease.

A preferred embodiment of the present invention is where the delivery vehicle is the combination of a modified unsaturated oil with a non-oxidizable oil. In even more preferred embodiments, the modified unsaturated oil is a substantially peroxidized unsaturated oil. For this embodiment, the ratio of modified unsaturated oil to non-oxidizable oil is from about from about 0.01:99.99 to about 90:10 (v/v), the total amount of both together being 100 percent, with particular reference to the range from about 10:90 to about 25:75 (v/v), and most particularly from about 10:90 to about 20:80 (v/v).

An example of this modified vehicle is where the modified unsaturated oil comprises modified cottonseed oil and the non-oxidizable oil comprises saturated coconut oil or a saturated coconut oil product (for example MIGLYOL 812). Modified cottonseed oil having a higher level of oxidation products as a result of heating natural cottonseed oil in the presence of oxygen is specifically contemplated as being a type of modified cottonseed oil. When the bioactive agent is CCFA, it is preferably combined with this modified vehicle such that the concentration of the CCFA in the composition ranges from between 50 mg/ml to 250 mg/ml and more preferably between 100 mg/ml to 200 mg/ml.

FIG. 1 presents a useful processing scheme for producing a sustained-release product of this embodiment. Natural (non-modified) cottonseed oil is added to a mixing tank (302) which is then heated and sparged with air to increase the peroxide value (304). The cottonseed oil is then cooled and sparged with nitrogen (306). The cottonseed oil at this point is deemed modified cottonseed oil. The vehicle (312) is then prepared by mixing 20 parts by volume of modified cottonseed oil (308) with 80 parts by volume of a saturated coconut oil or saturated coconut oil product, for example Miglyol 812. (310). Drug (bioactive substance, for example CCFA) is added to the vehicle (314) and the mixture is purged with nitrogen (316). The purged mixture is heated and the release rate of the drug is monitored using an in process assay procedure to determine when the desired release rate is achieved. At this point the heating is terminated (318) and the mixture is cooled (320), filled into vials (322) and terminally sterilized by gamma irradiation (324) and released against final specifications (326).

Revisiting the process of FIG. 1, it is contemplated that sustained-release formulations of other embodiments can be achieved by alternate routes within the disclosed process. For example, in one such process, drug is added to a non-modified unsaturated oil and directly subjected to terminal irradiation to modify the unsaturated oil and produce a sustained-release vehicle. In another, the process is terminated after fill and without terminal sterilization. It is an important aspect of the invention that not all processing steps are required to result in a sustained-release preparation in every protocol. However, in accordance with the present invention some type of chemical, physical, or mechanical modification or any combination of the above is required.

In addition to the instant inventive vehicle of the instant invention, the compositions of this invention can be employed in admixture with conventional excipients, i.e., pharmaceutically acceptable organic or inorganic carrier substances suitable for parenteral, enteral (e.g., oral or inhalation) or topical application which do not deleteriously react with the active compositions. Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compositions. They can also be combined where desired with other active agents, e.g., vitamins. In specific embodiments, the liquid carrier may additionally contain a thickening agent, for example, beeswax, hard paraffin or cetyl alcohol. Also noted as optional additives are benzyl alcohols, polyethylene glycols, viscous paraffin, perfume oil, and fatty acid esters.

The inventive compositions are useful for human and veterinary medicine.

More specifically, the compositions of the present invention can be used to treat humans, food animals or companion animals. This includes, but is not limited to the following: food animals such as cattle, swine, sheep, goats and deer; companion animals such as horses, cats and dogs; poultry; or humans. The amount of inventive composition to be administered is that which will deliver the bioactive agent in an amount and for a duration to provide a therapeutic benefit necessary to treat or prevent a disease without causing toxicity problems to the patient. The specific amounts to be selected are deemed to be within the skill of the artisan. For example, when CCFA is selected as the bioactive agent, it is administered in unit dosage form for intramuscular or subcutaneous administration comprising about 0.5 to about 10.0 mg CCFA/kg body weight of patient with preferred ranges of about 4.4-6.6 mg/kg for cattle, and 5.0-7.5 mg/kg for swine. To the extent necessary for completion the dosages as described in U.S. Pat. No. 5,721,359 and U.S. Pat. No. 6,074,657 are expressly incorporated by reference.

Administration of the composition is contemplated to include chronic, acute or intermittent regimens, and any mode where liquid administration is feasible may be selected. The compositions of the present invention can be administered parenterally (for example, subcutaneous, intramammary, intravenous, intraperitoneal or intramuscular injection), topically (including but not limited to surface treatment, transdermal application, and nasal application), intravaginally, orally, or rectally.

For oral therapeutic administration, the composition may be administered in the form of capsules, elixirs, suspensions, syrups, and the like. Such compositions and preparations should, typically, contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active composition may be incorporated into sustained-release preparations and devices such as the osmotic release type devices developed by the Alza Corporation under the OROS trademark.

For parenteral application, the compositions can be administered intravenously or intraperitoneally, by infusion or injection. In one embodiment where CCFA is the bioactive agent, subcutaneous ear injection in accordance with U.S. Pat. No. 6,074,657 is an appropriate mode of administration. Intramuscular, intramammary and general subcutaneous administration is also specifically contemplated.

For topical administration, the composition may be applied in the form of drops (for example to treat diseases or infections of the eye), or for skin application in the form of spreadable pastes, gels, ointments, soaps, and the like. The resultant liquid compositions can additionally be applied from absorbent pads or suppositories, used to impregnate bandages and other dressings, or sprayed onto the affected area using pump-type or aerosol sprayers.

It will be appreciated that the actual preferred amounts of active compositions in a specific case will vary according to the specific compositions being utilized, the particular compositions formulated, the mode of application, and the particular situs and organism being treated. Dosages for a given host can be determined using conventional considerations, e.g., by customary comparison of the differential activities of the subject compositions and of a known agent, e.g., by means of an appropriate, conventional pharmacological protocol.

An important aspect of the present invention is that by performing the modification to the carrier vehicle, the in vivo performance of the bioactive substance can be entirely controlled and predictable. To this extent, while not wishing to be bound to any particular scientific theory, the performance of the bioactive substance is "locked in" immediately post manufacture. As such, the performance of the bioactive substance in vivo is comparable (i.e., the active is released to the host such that it remains in the host at a therapeutically effective level for a desired period of time) from the time of manufacture for many months of storage time. As an example, the performance of the bioactive administered in vivo 30 days, 60 days, 90 days, 180 days, 360 days or 720 days after manufacture is comparable to the performance just after manufacture. In contrast, in prior formulations when unmodified vehicles are selected, the in vivo performance is not as readily predictable as the performance of the bioactive composition immediately after manufacture and may differ from its performance some time after manufacture. The reproducibility, predictability and consistent performance obtained when using the composition of the present invention provides a clear advance in the art.

While the present invention is primarily directed to sustained-release delivery vehicles, it is also expressly contemplated that for certain bioactive substances advantages can be obtained without the vehicle being a sustained-release one. For example, the chemical or physical stability of the final formulation could be improved. Further, for parenteral formulations the compositions of this invention may provide reduced injection site irritation for certain tissue irritating bioactive substances. For oral formulations compositions of this invention could possibly provide protection against stomach irritation by certain bioactive substances, may help mask the taste of poorly palatable drugs, and might be used to target delivery of certain drugs (i.e. where it's desired that absorption of the active medicament occur lower in the G.I. tract, rather than in the stomach—for greater efficacy, to target certain disease conditions, etc.) For intramammary formulations compositions of this invention could possibly provide reduced udder irritation, and might prevent or reduce systemic absorption of the drug from the udder, leaving more medicament at the site of the infection, thus improving efficacy and increasing chances for reduced slaughter times.

The invention is further described in the following non-limiting examples.

Preparation 1

Cottonseed Oil Modification

A substantially peroxidized unsaturated is prepared from natural cottonseed oil. 105 parts by volume of natural cottonseed oil are added to a vessel having a steam jacket for heating. Steam is applied to the jacket to heat the oil to between about 85 and about 100° C. Air is bubbled through the oil while it is agitated. The flow rate of the air varies from about 1 standard cubic foot per hour (SCFH)/liter to 20 SCFH/liter. Agitation is such that the temperature of the oil remains constant over the time period of heating. The oil is heated for a time and at a temperature necessary to achieve a peroxide value as measured by the method of the US Pharmacopea (USP 24 NF 19 at page 1870) or by AOCS method 8-53 and then cooled, transferred to a different container and stored under nitrogen conditions. To achieve a peroxide value of about 10, at a temperature of about 89° C. the oil is heated for about 9 hours, at a temperature of about 100° C. the oil is heated for about 3 hours, and at a temperature of about 105° C. the oil is heated for about 2.3 hours. To achieve a peroxide value of about 40, at a temperature of about 100° C. the oil is heated for about 6.75 hours, and at a temperature of about 105° C. the oil is heated for about 5.5 hours. To achieve a peroxide value of about 80, at a temperature of about 105° C. the oil is heated for about 8 hours. The relationship between the time and temperature of the oil as compared to its peroxide value is considered to be linear and one skilled in the art could achieve a desired peroxide value depending on the time and temperatures selected for processing.

Example 1

(i) 10 parts by volume of the modified cottonseed oil prepared according to Preparation 1 and having a peroxide value of between about 10-40 are mixed with 90 parts by volume of Miglyol 812 to form a carrier vehicle.

(ii) 0.1 parts by weight of CCFA are added and mixed for 1-3 hours to form a uniform suspension such that the concentration of CCFA is 100 mg/ml.

(iii) The suspension is heated to about 85-110° C. for about 2-20 hours and permitted to cool.

(iv) The suspension is packaged and sterilized with gamma radiation.

The resulting product is a stable, sustained-release formulation of CCFA having a concentration of 100 mg/ml.

Example 2

The procedure of Example 1 is repeated except that in step (i) the ratio of modified cottonseed oil to Miglyol 812 is 20:80, and in step (ii) the amount of CCFA added is such that the concentration of CCFA is 200 mg/ml. The resulting product is a sustained-release formulation of CCFA having a concentration of 200 mg/ml.

Example 3

The procedure of Example 2 is repeated except that steps (iii) and (iv) are replaced with the step of filling vials with the suspension and terminally heating the packaged suspension to 85-110° C. for about 3-14 hours and allowing the vials to cool. The resulting product is a stable, sustained-release formulation of CCFA having a concentration of 200 mg/ml.

Example 4

The procedure of Example 3 is repeated except that the following step (i) is substituted for the identical step in Example 3 and in step (ii) the amount of CCFA added is such to obtain a final concentration of 100 mg/ml.

(i) Natural peanut oil is modified by heating it to 90-100° C. for a period of 1-10 hours to yield a composition having a peroxide value of between 10-80. 1 part of the modified peanut oil by volume is mixed with 99 parts by volume of Miglyol 810 for 1-3 hours.

The resulting product is a stable, sustained-release formulation of CCFA having a concentration of 100 mg/ml.

Example 5

A formulation is prepared as set forth in Example 1 except that the following step (i) is substituted for the identical step in Example 1, in step (ii) the amount of CCFA added is such to obtain a final concentration of 250 mg/ml, and step (iii) is omitted.

(i) Natural corn oil is modified by heating it to 90-100° C. for a period of 1-10 hours to yield a composition having a peroxide value of between of 5-50. 5 parts by volume of this is mixed with 95 parts by volume of Miglyol 829 for 1-3 hours to yield a carrier vehicle.

Example 6

(i) 40 parts by volume of modified sesame oil prepared using the heat treatment according to Preparation 1 and having a peroxide value of between about 4-60 are mixed with 60 parts by volume of isopropyl myristate to form a carrier vehicle.

(ii) 0.15 parts by weight of ceftiofur crystalline free acid are added and mixed for 1-3 hours to form a uniform suspension such that the concentration of CCFA is 150 mg/ml.

(iii) The suspension is packaged and heated to 85-110° C. for about 3-14 hours and permitted to cool.

The resulting product is a stable, sustained-release formulation of CCFA having a concentration of 150 mg/ml.

Example 7

(i) 15 parts by volume of safflower oil are mixed with 85 parts by volume of Miglyol 840 to form a carrier vehicle.

(ii) 0.30 parts by weight of CCFA are added and mixed for 1-3 hours to form a uniform suspension such that the concentration of CCFA is 300 mg/ml.

(iii) The suspension is packaged subjected to microwave radiation to modify the safflower oil and permitted to cool.

The resulting product is a stable, sustained-release formulation of CCFA having a concentration of 300 mg/ml.

Example 8

(i) 100 parts by volume of palm oil are prepared using the heat treatment according to Preparation 1 to have a peroxide value of between about 10-100 to form a carrier vehicle.

(ii) 0.10 parts by weight of ceftiofur crystalline free acid are added and mixed for 1-3 hours to form a uniform suspension such that the concentration of CCFA is 100 mg/ml.

(iii) The suspension is heated to 85-110° C. for about 2-20 hours and permitted to cool.

(iv) The suspension is packaged and sterilized with gamma radiation.

The resulting product is a stable, sustained-release formulation of CCFA having a concentration of 100 mg/ml.

Testing of Inventive Compositions

Cows suffering from either bovine respiratory disease or an anaerobic infection of the interdigital space are injected with any of the compositions of Examples 1-8 such that the level of administration of CCFA is between about 4.4 to about 6.6 mg CCFA/kg animal body weight. Administration is by subcutaneous injection in the neck or subcutaneous injection in the ear as described in U.S. Pat. No. 6,074,657. The concentration of effective CCFA metabolites in the blood plasma of the cows rises to at least 0.2 μg/ml within one hour of administration and remains at or above this level for at least 80 to about 140 hours. Only one administration of CCFA is required for the treatment regimen.

Having described the invention in detail and by reference to the preferred embodiments thereof, it will be apparent that modifications and variations are possible without departing from the scope of the appended claims.

What is claimed is:

1. A composition comprising:
   (a) crystalline ceftiofur free acid; and
   (b) a modified liquid vehicle, said vehicle comprising;
      i) a modified unsaturated oil having a peroxide value of between about 10 to about 600 milliequivalents (mEq) of peroxide per 1000 grams of oil and optionally,
      ii) a saturated oil;
   wherein said modified unsaturated oil comprises corn oil, peanut oil, sesame oil, olive oil, palm oil, safflower oil, soybean oil cottonseed oil, rapeseed oil, sunflower oil, a modified oxidizable synthetic oil, or mixtures thereof; wherein said saturated oil comprises coconut oil; wherein the saturated oil may be present at a level such that the ratio of modified unsaturated oil to saturated oil is from about 0.01:99.99 to about 90:10 (v/v).

2. The composition according to claim 1 wherein said modified liquid vehicle comprises a modified unsaturated oil and a saturated oil.

3. The composition according to claim 1 wherein said modified liquid vehicle comprises a mixture of a modified unsaturated oil with either a non-modified saturated oil or a non-modified unsaturated oil.

4. The composition according to claim 1 wherein said modified unsaturated oil comprises modified cottonseed oil.

5. The composition according to claim 1 wherein said modified liquid vehicle is a mixture of modified cottonseed oil and saturated coconut oil.

6. The composition according to claim 1 wherein said modified liquid oil includes a substantially peroxidized unsaturated oil.

7. A composition comprising crystalline ceftiofur free acid, modified cottonseed oil and coconut oil.

8. The composition according to claim 7 wherein the ratio by volume of modified cottonseed oil to coconut oil is between 0.01:99.99 to 30:70.

9. The composition according to claim 8 wherein the ratio by volume of modified cottonseed oil to coconut oil is between 10:90 to 20:80.

10. The composition according to claim 7 wherein the concentration of crystalline ceftiofur free acid in said composition ranges from 50 mg/ml to 250 mg/ml.

11. The composition according to claim 10 wherein the concentration of crystalline ceftiofur free acid in said composition ranges from about 100 mg/ml to about 200 mg/ml.

12. A composition consisting essentially of crystalline ceftiofur free acid, modified cottonseed oil and coconut oil wherein the concentration of crystalline ceftiofur free acid in said composition ranges from about 100 mg/ml to about 200 mg/ml and the ratio by volume of modified cottonseed oil to coconut oil is between about 10:90 to about 20:80.

13. A composition comprising:
   (a) crystalline ceftiofur free acid; and
   (b) a modified liquid vehicle, said vehicle comprising;
      i) a modified unsaturated oil comprising a substantially peroxidized unsaturated oil having a peroxide value of between about 10 to about 600 milliequivalents (mEq) of peroxide per 1000 grams of oil and,
      ii) a saturated oil
   wherein the unsaturated oil is modified before it is combined with the saturated oil to form a modified liquid vehicle.

* * * * *